United States Patent [19]

Haas

[11] 4,439,148
[45] Mar. 27, 1984

[54] ORTHODONTIC APPLIANCES AND METHOD OF TREATMENT

[76] Inventor: Andrew J. Haas, 1234 Portage Trail, Cuyahoga Falls, Ohio 44221

[21] Appl. No.: 349,993

[22] Filed: Feb. 18, 1982

[51] Int. Cl.³ .............................................. A61C 7/00
[52] U.S. Cl. ............................................ 433/5; 433/7
[58] Field of Search ........................................ 433/5, 6

[56] References Cited

U.S. PATENT DOCUMENTS

| | | | |
|---|---|---|---|
| 1,773,588 | 8/1930 | Linde | 32/14 |
| 2,259,160 | 10/1941 | Glaser | 32/14 |
| 2,880,509 | 4/1959 | Strickler | 32/14 |
| 2,983,046 | 5/1961 | Jenkins | 433/5 |
| 3,186,089 | 6/1965 | Asher | 32/14 |
| 3,230,621 | 1/1966 | Lindquist et al. | 32/14 |
| 3,286,576 | 11/1966 | West | 84/466 |
| 3,295,519 | 1/1967 | Gerber | 128/136 |
| 3,311,978 | 4/1967 | Haas et al. | 32/14 |
| 3,314,151 | 4/1967 | Rubin | 32/14 |
| 3,327,580 | 6/1967 | Herweg | 84/453 |
| 3,340,613 | 9/1967 | De Woskin | 32/14 |
| 3,478,742 | 11/1969 | Bohlmann | 433/6 |
| 3,638,313 | 2/1972 | Cervera | 32/14 |
| 3,835,540 | 9/1974 | Biederman | 32/14 |
| 3,997,971 | 12/1976 | Moss | 32/14 |
| 4,195,046 | 3/1980 | Kesling | 264/16 |
| 4,202,100 | 5/1980 | Forster | 433/7 |
| 4,229,165 | 10/1980 | Kurz | 433/24 |
| 4,245,986 | 1/1981 | Andrews | 433/5 |

Primary Examiner—Robert Peshock
Attorney, Agent, or Firm—Reese Taylor

[57] ABSTRACT

Multiple purpose orthodontic appliances for correcting the malocclusion of teeth in all planes; correcting jaw discrepancies in all planes of space; stimulating maximum development of dental arches; orthopedically widening the upper jaw bone; and stimulating development of the orofacial musculature and a method of employing the applicances includes the utilization of a face bow with suitable plastic shields affixed thereto to provide orthopedic treatment as well as the usual orthodontic correction provided by the face bow itself. The face bow includes interconnected outer and an inner arch wires and in one form, the shield is positioned in the anterior area of the inner arch wires so as to provide labial or anterior pressure on the lip muscles. In a second form, the shields are disposed along the sides of the inner arch wires to provide buccal or lateral influence on the cheek muscles. In a third form, the shield covers both the anterior and lateral area of the inner arch wires so as to provide both labial and buccal pressure. A modified form of the invention includes the provision of a centrally located air passage or aperture in the anteriorly disposed shield to facilitate oral breathing while wearing the appliance. Another form of the invention includes the provision of superior and inferior hooks on the inner surface of the shields to enable the appliance to provide fairly specialized corrective orthodontic forces. Still another form of the invention includes a spring loaded arch wire and shield combination designated for entirely interoral use.

23 Claims, 15 Drawing Figures

ORTHODONTIC APPLIANCES AND METHOD OF TREATMENT

FIELD OF THE INVENTION

This invention relates, in general, to orthodontic apparatus and treatment methods and relates, in particular, to appliances and a method for providing both orthodontic correction and orthopedic correction.

DESCRIPTION OF THE PRIOR ART

The prior art known to applicant generally includes what is commonly called a face bow or night brace. Such a face bow or night brace is generally composed of inner and outer arch wires having a U-shaped or arcuate configuration and joined together at their center portions in a suitable manner. The inner arch wire is commonly secured to selected teeth by attachment bands while the outer arch wire serves as an attachment means to secure the face bow to the head or neck or both by means of externally applied straps or elastic members. In this way, pressure is applied and malocclusion of the teeth can be corrected. Examples of face bows of this general type may be seen in Haas U.S. Pat. No. 3,311,978; Asher U.S. Pat. No. 3,186,089; Lindquist U.S. Pat. No. 3,230,621; Rubin U.S. Pat. No. 3,314,151; De Woskin U.S. Pat. No. 3,340,613; Cervera U.S. Pat. No. 3,638,313; Moss U.S. Pat. No. 3,997,971; Forster U.S. Pat. No. 4,202,100; Kurz U.S. Pat. No. 4,229,165; and Andrews U.S. Pat. No. 4,245,986.

Also, although not necessarily orthodontic corrective devices, the patent prior art does disclose some devices for engaging the lips and perhaps cheeks of the wearer. Examples of this art in the orthodontic field can be seen in Glaser U.S. Pat. No. 2,259,160 and Strickler U.S. Pat. No. 2,880,509. Non-orthodontic examples of this art can be seen in West U.S. Pat. No. 3,286,576 and Gerber U.S. Pat. No. 3,295,519.

While the orthodontic prior art referred to above, both in the patent field and in general use, is presumably suitable for correcting the malocclusion of teeth by affixing intraoral appliances, such as the face bows, to varying numbers of teeth, it has not been considered possible, up to the present time, to combine that adjustment and correction of the teeth themselves with an appliance and treatment method which would correct jaw discrepancies in all planes; stimulate maximum development of the dental arches; and stimulate maximum development of the orofacial musculature.

The present invention is believed, however, to present an appliance and a treatment method which is capable of accomplishing all of these objectives.

BRIEF SUMMARY OF THE INVENTION

It has been found that with the appliance and method of this invention that the following objectives can be accomplished:
1. Correcting the malocclusion of teeth in all planes.
2. Correcting jaw discrepancies in all planes.
3. Stimulating lateral growth of the maxillary jaw beyond its inherited growth potential.
4. Stimulating maximum development of the dental arches (teeth and bone support).
5. Stimulating maximum development of the orofacial musculature (the lips and cheeks).

Accordingly, it has been found that if a face bow having arcuate outer and inner arch wires which are joined together adjacent their midpoints is modified by the addition of a suitable plastic shield in appropriate places, that the aboveidentified objectives can be met.

Essentially, the first objective above-cited, namely correcting the malocclusion of the teeth, can basically be accomplished by utilization of the face bow itself by affixing the inner arch wire to varying numbers of teeth and applying pressure by means of the external straps secured to the face bow or outer arch wire. Utilizing the reciprocal action of the stretch reflex of the orofacial muscles to move teeth is believed to be a new concept and by incorporating the shields on the basic face bow structure the usual action of the face bow can be augmented.

Thus, if the shields are secured to the inner arch wire in the anterior or forward area, they will be capable of exerting labial pressure, i.e., pressure on the lips. This will, in turn, reduce the force of the lip muscles against the teeth. This will also stimulate development of the dental arches as the relatively stronger tongue will influence anterior development of the arch and will primarily influence the muscles of the lips and tissues of the anterior portion of the mouth to full growth potential.

It has also been found that, alternatively, the shields can be placed on the sides of the inner arch wire so as to apply buccal or lateral pressure against the cheeks. This, again, will reduce the force of those muscles against the teeth, promoting optimal lateral growth of the dental arches and the cheek muscles themselves.

It has further been found that these two concepts can be combined with a shield which extends from the anterior portion of the inner arch wire along the trailing legs thereof so as to exert both labial and buccal forces simultaneously. This creates pressures which promote maximum growth and development of the orofacial muscles (lip and cheek) and by the reciprocal reaction of the stretch reflex of the musculature, the molar connecting teeth are moved to more favorable positions.

Furthermore, it has been discovered that the inner surfaces of the shields themselves can be provided with superior and inferior hooks which provide attachment points for elastic bands used to exert forces in a lineal posterior direction to close the spaces in the upper anterior teeth or in a vertical direction to lift or cradle the teeth to prevent their eruption in a growing individual or both. Thus, the inferior hooks can provide a horizontal correction of the anterior teeth and the superior hooks can provide a vertical correction of the incisor teeth.

It has also been found possible to improve or at least facilitate breathing by the wearer if the anteriorly disposed shield is provided with a central aperture or passageway for breathing purposes. This feature has been found particularly helpful where the patient has acute or chronic blockage of the nasal airway.

Finally, an entirely intraoral variation of the invention has been found to provide most of the qualities of the forms of the invention just described including inducing lateral orthopedic growth although lacking some orthopedic potential in the anterior-posterior plane. This variation can be worn entirely within the mouth thereby enhancing the aesthetic effects thereof while accomplishing essentially the desired objectives. In this case, a single arch wire is provided with a shield. Anchoring means such as bands are provided at the ends of the legs of the arch wire so that they may be secured to the teeth. Between these anchoring means and the ends of the shield are provided springs which are in compression and will provide pressure against the lip muscles through the shield.

The muscles so stimulated reflexively by the compressed springs apply a posterior force to the anchoring molar teeth causing those teeth to move posteriorly. In a growing child the stretching of the lip stimulates growth of these structures while encouraging the anterior teeth to move forward as a consequence of the altered muscle balance between the tongue and lip. The teeth move toward the least resistance, namely, the stretched and growing lip musculature. Thus the anterior-posterior relationship of the two dental arches is corrected while space is gained for tooth alignment in the upper arch.

Accordingly, production of improved appliances and a method for their use of the character above described becomes the principal object of this invention with other objects thereof becoming more apparent upon a reading of the following brief specification, considered and interpreted in view of the accompanying drawings.

BRIEF DESCRIPTION OF THE PREFERRED EMBODIMENTS

As noted above, in orthodontic treatment it is essentially desirable to correct the alignment or occlusion of the teeth. Also, as noted above, this is frequently accomplished by utilization of a face bow which will (1) cause the jaws to grow into more normal relationship and (2) make space available for teeth. The fine tuning or precision alignment of teeth is accomplished by means of braces and arch wires attached to many or all teeth. The face bow is the motor force for the intraoral fixed appliances.

As also noted above, however, it is also desirable, in most instances, to improve the over all environment of the teeth, or in other words, to improve the anatomical structure of the mouth itself. In order to do so, it is desirable to correct jaw discrepancies; correctly develop the dental arches; and stimulate maximum development of the orofacial musculature. The present invention is intended to accomplish all of these objectives.

Figure 1:
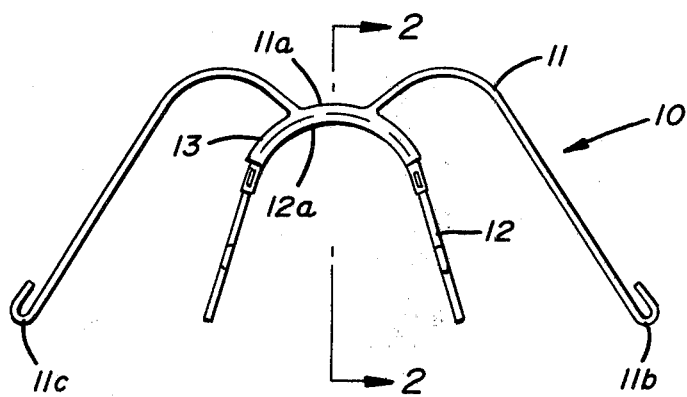
FIG. 1 is a top plan view of one form of the appliance of this invention.

Turning then to the drawings for some of the specific appliances employed, attention is first called to FIG. 1 of the drawings wherein the face bow, generally indicated by the numeral 10, includes an outer arch wire 11 and an inner arch wire 12. These are generally arcuate or U-shaped in plan and joined together in the arcuate central or anterior regions 11a and 12a.

For purposes of this invention, it is not relevant how the wires 11 and 12 are joined together. Thus, they could be made unitary or they could be made in separate pieces and welded, soldered, brazed, or otherwise secured together as is well known in the art.

Continuing then with a general description of the face bow 10, it will be noted that the opposed ends of outer arch wire 11 terminate in opposed hooks 11b,11c. These hooks are conventional and are intended to be fastened to a strap 13 (see FIG. 3) which fits around the head of the wearer in order to apply tension. This structure is not illustrated in great detail herein since it is entirely conventional and can be seen in several of the prior art patents referred to herein.

Referring again to FIG. 1, however, it will be noted that, in addition to the usual face bow structure, a shield 13, which is either of rigid or semi-rigid plastic or similar material, is secured to the inner arch wire 12 and extends basically along the arcuate or anterior area thereof projecting above and below the plane of the wire. In other words, this shield is disposed in the anterior area of the mouth when the device is worn. When the device is employed, of course, the shield 13 will bear against the lips and will exert an influence on the muscles and tissues of the anterior area of the mouth to stretch them and permit maximum enlargement or growth. Such an influence on the muscles will also reduce their force on the teeth thus promoting optimal anterior growth of the dental arches. This orthodontic correction occurs simultaneously with the frequently required orthopedic correction.

To accomplish the orthopedic growth of the maxilla in the lateral dimension, the shield 13 and the inner arch wire 12 may be fitted 6 to 10 millimeters wider than the dental arch. The teeth thus become handles by which the two bones of the maxilla are moved apart. New bone is deposited in the suture between the two bones and, thus, a permanent widening is assured.

Figure 4:
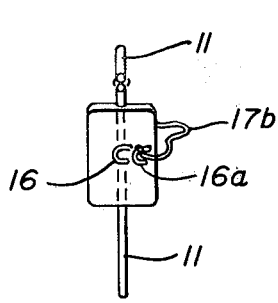
FIG. 4 is a sectional view taken along the line 4—4 of FIG. 3.
Figure 3:
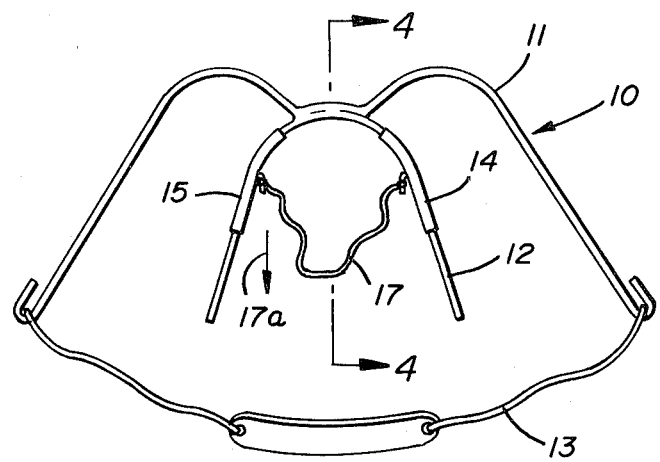
FIG. 3 is a top plan view of a modified form of the invention.

Turning then to the modification of FIGS. 3 and 4, it will be noted that, again, the face bow is generally indicated by the numeral 10 and that the outer and inner arch wires 11 and 12 are similar to those of FIG. 1. However, here the shield structure takes the form of a pair of shields 14 and 15 disposed along the legs of the inner arch wire. These will, of course, apply pressure against the cheek muscles.

This form of the invention exerts a primary influence on those muscles and connective tissues and promotes optimal lateral growth of the dental arches.

Figure 5:
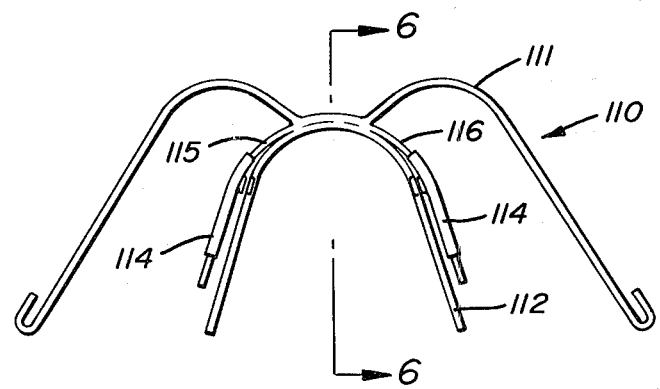
FIG. 5 is a top plan view of still another modified form of the invention.

FIG. 5 of the drawings shows a further modified form of the invention in which the face bow 110 includes an outer arch wire 111 and an inner arch wire 112. However, this form of the invention also includes a pair of opposed auxiliary support wires 115,116 each of which carries a shield 114. This form of the invention will operate similarly to the form of the invention illustrated in FIGS. 3 and 4 of the drawings differing therefrom essentially only in the fact that instead of the shields being mounted directly on the inner arch wire 12 of FIG. 3, they are mounted on the auxiliary support wires 115 and 116.

Figure 2:
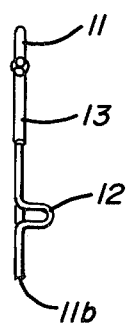
FIG. 2 is a sectional view taken along line 2—2 of FIG. 1.
Figure 8:
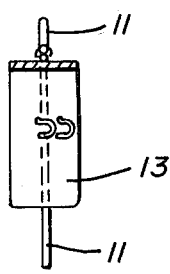
FIG. 8 is a sectional view taken along the line 8—8 of FIG. 7.
Figure 7:
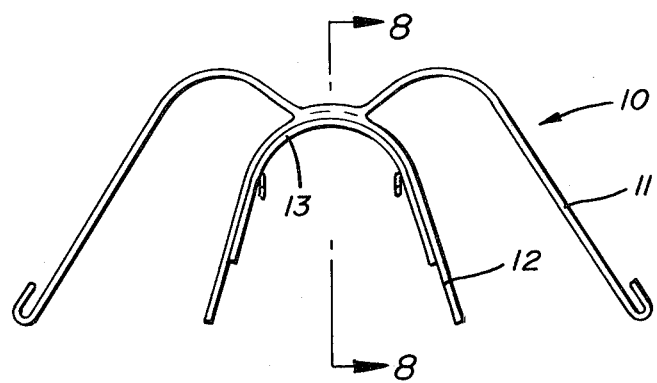
FIG. 7 is a top plan view of the still further modified form of the invention.
Figure 6:
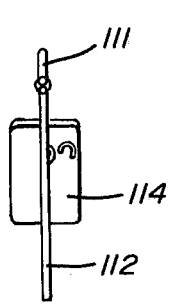
FIG. 6 is a sectional view taken along the line 6—6 of FIG. 5.

FIGS. 7 and 8 of the drawings illustrate a further modification of the invention in which the face bow 10 again consists of the outer arch wire 11 and the inner arch wire 12. Here, however, the shield structure 13 covers not only the anterior curved or arcuate area of the arch wire 12, as is the case in FIGS. 1 and 2, but extends along the opposed legs so that essentially the form of the invention illustrated in FIGS. 7 and 8 of the drawings is a combination of the principles illustrated in FIGS. 1 through 5. In this instance, pressure will be exerted against both the lip muscles and the cheek muscles.

Figure 10:
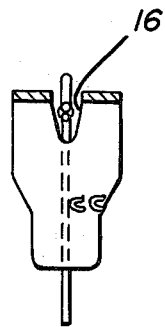
FIG. 10 is a sectional view taken along the line 10—10 of FIG. 9.
Figure 9:
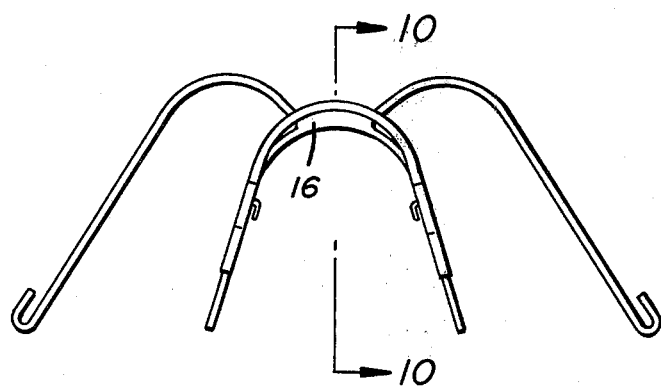
FIG. 9 is a top plan view of still a further modification of the invention.

FIGS. 9 and 10 of the drawings illustrate yet another form of the invention in which an air passageway 16 is provided in the central area of the shield. This feature is sometimes desirable when the patient has acute or chronic blockage of the nasal airway and facilitates oral breathing.

Figure 11:
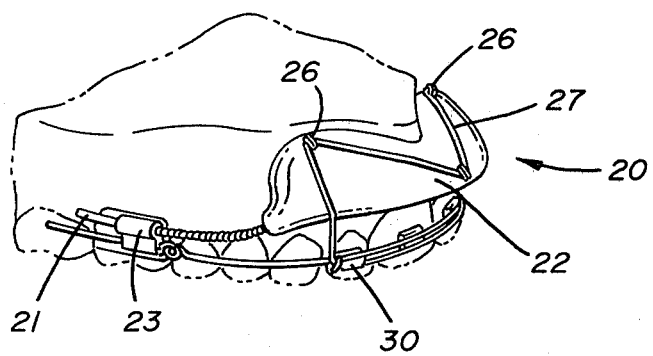
FIG. 11 is a perspective view of the entirely interoral form of the invention.
Figure 13:
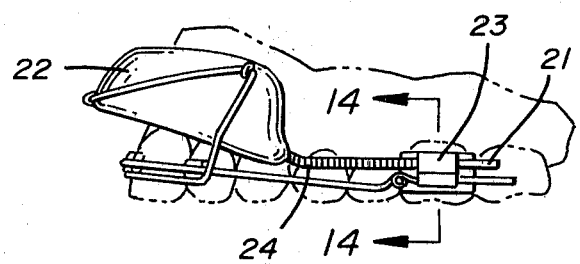
FIG. 13 is a side elevational view of the form of the invention shown in FIG. 11.
Figure 12:
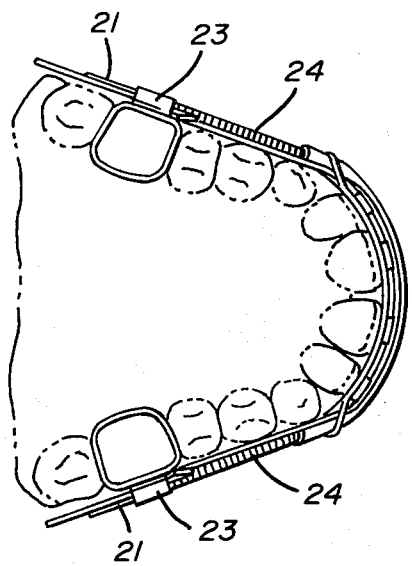
FIG. 12 is a occlusal view of the form of the invention illustrated in FIG. 11.
Figure 15:
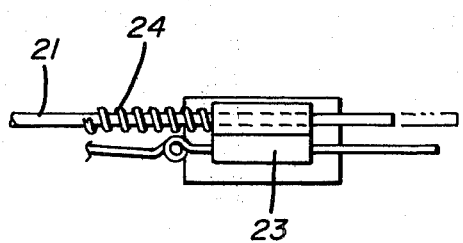
FIG. 15 is an enlarged detailed view of the spring tension means of the form of the invention of FIGS. 11 through 14.
Figure 14:
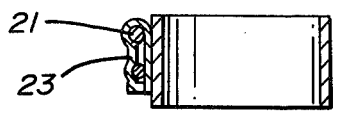
FIG. 14 is a sectional view taken along the line 14—14 of FIG. 13.

FIG. 11 shows yet another form of the invention which is essentially an entirely interoral activator employing the general principles of the form of the invention illustrated in FIGS. 1 through 10 but providing an improved aesthetic advantage and thus improved acceptability by patients.

Thus, this form of the invention is generally indicated by the numeral 20 and includes an arcuate wire support 21 carrying, in its anterior area, a shield 22. The distal ends of the legs of the wire 21 carry attachment means or bands 23,23 and a coil spring 24 is disposed on each leg between the ends of the shield 22 and the attachment means 23. The attachment means, of course, are designed to be attached directly to the teeth of the wearer and to be crimped or otherwise secured to the arch wire 21. This feature permits the distance between the point of attachment and the ends of the shield to be controlled and thus permits adjustment of the spring tension.

In this form of the invention, the shield 22 is constructed to fit the anatomic structure of the maxillary labial and buccal alveolar plates and soft tissue overlying them. This shield 22 would be made on a working model which would in turn be made from an impression that completely defines the relevant area of the specific patient.

The coil springs 24 are under mild compression and cause the fitted shield to move forward against the muscles of the lips. Such movement will stimulate the growth of those muscles and cause the coil springs 24 to deliver a force to the molars. In this fashion, the posterior teeth are held in place or moved posterially while the anterior teeth are free to move forward. Lessening the labial pressure from the lip muscles, relatively speaking, will increase the pressure from the tongue and thus result in the desirable forward expansion of the teeth.

If desired, a vertical slit can be made at the center portion of the shield 22 to permit lateral activation. In this fashion, an anterior flatening of the shield 22 of the activator is caused which, in turn, causes the buccal aspects of the wire to expand. This results in the desired muscular orthopedic and orthodontic changes already described in connection with the forms of the invention illustrated in FIGS. 1 through 10.

Finally, it will be noted that the shields of all of the various forms of the invention also include hooks which are imbedded or otherwise secured to the inner faces thereof.

Referring, for example, to FIGS. 3 and 4 of the drawings, superior hooks 16 and inferior hooks 16a are illustrated. In practice, these hooks would be provided on the shields in all forms of the invention and their selective usage would be determined by the clinician depending upon the specific treatment required for a specific patient.

For example, the primary purpose of the lower or inferior hooks 16 is to provide a point of attachment for an elastic band. The gently stretched elastic 17 would engage cenventional brackets affixed to the upper incisor teeth to exert a posterior lineal force in the direction of arrow 17a against the anterior teeth causing these teeth to move posteriorly. This has been found to be a very effective means of closing spaces between the upper anterior teeth. The actual engagement between elastic 17 and the brackets is not illustrated in FIGS. 1 through 10 but the concept is believed sufficiently described to permit its practice by one skilled in the art (see also FIGS. 11 through 15).

The primary purpose of the upper or superior set of hooks 16a is to provide a point of attachment for an elastic band 17b so that it will lie superior to the anterior teeth. The elastic can then be stretched in an inferior direction to engage the interoral appliance, such as conventional brackets, attached to those anterior teeth. This provides a vertical force to the upper incisors and effectively lifts those teeth and prevents their eruption in a growing individual or, if desired, will cause a depression of those teeth in a non-growing individual.

It is also possible to employ a combination of these methods, e.g., an inferior hook 16a on one side and a superior hook 16 on the other to achieve a differential vertical intrusion of the teeth and bring the teeth into a plane parallel to that of the lip.

It is also sometimes desirable to gain more depression of the upper incisors on one side of the dental arch than on the other such as in cases where these teeth do not follow a line parallel with the upper lip line. In such an instance, the elastic band can be attached to the superior hook on the side requiring the greater degree of depression and to an inferior hook on the side requiring the lesser amount.

As noted above, the hooks 16 and 16a are intended to be provided on all forms of the invention with the only significant difference being that in the form of the invention illustrated in FIG. 11, the hooks are mounted on the outer face of the shield since the inner face is fitted to the upper jaw.

Thus, with this form of the invention, it is only possible to utilize elastic 27 in the superior direction which is the most common requirement anyway.

It will be noted that the elastic 27 is engaged with the hooks 26,26 and then engaged with the conventional brackets 30 on the teeth. This will, of course, provide movement in the superior direction.

While a full and complete description of the invention has been set forth in accordance with the dictates of the Patent Statutes, it should be understood that modifications can be resorted to without departing from the spirit hereof or the scope of the appended claims.

Thus, the shields have been referred to herein as a "suitable plastic" shield and it should be understood that the invention is not intended to be limited to any specific material. Any material which has sufficient body to elicit the stretch reflex but is sufficiently soft to avoid cutting or lacerating the tissue will suffice.

What is claimed is:

1. An orthodontic face bow appliance, comprising:
   (A) an outer arch wire having an arcuate central portion;
   (B) an inner arch wire having an arcuate central portion and being interconnected to said outer arch wire adjacent their arcuate central portions;
   (C) a shield carried by said inner arch wire and projecting only in a vertical plane above and below the plane of said arch wires to engage and exert pressure on the soft tissues of the mouth;
      1. Whereby orthodontic correction of the teeth and orthopedic correction of the structure of the mouth are achieved simultaneously,
   (D) means carried by said outer wire for attachment of said appliance to the head of the user thereof.

2. The appliance of claim 1 wherein said shield has an outer and an inner face; a plurality of hooks being disposed on the inner face thereof.

3. The appliance of claim 2 wherein said hooks are disposed in superior and inferior positions on said shields.

4. The appliance of claim 1 wherein said shield includes an elongate plastic member extending along said inner arch wire an extent equidistant from the midpoint of the arcuate central portion thereof.

5. The appliance of claim 1 wherein said inner arch wire includes opposed legs extending away from said arcuate central portion thereof; and said shield includes a pair of elongate plastic members secured to said legs.

6. The appliance of claim 1 wherein said inner arch wire includes opposed legs extending away from said arcuate central portion thereof; and said shield includes an elongate plastic member extending along said arch wire throughout said arcuate central portion and along at least a portion of said legs.

7. An orthodontic face bow appliance, comprising:
   (A) an outer arch wire having an arcuate central portion;
   (B) an inner arch wire having an arcuate central portion;
   (C) said inner and outer arch wires being interconnected adjacent their arcuate central portions;
   (D) a pair of auxiliary support wires
      (1) disposed between said outer and inner arch wires and
      (2) projecting from opposed sides of the arcuate central portions of said outer and inner arch wires;
   (E) shield means carried by said support wires; and
   (F) means carried by said outer wire for attachment of said appliance to the head of the user thereof.

8. The appliance of claim 7 wherein said shield means include inner and outer faces; and a plurality of hooks being disposed on said inner faces.

9. The appliance of claim 7 wherein said shield includes a pair of elongate plastic members secured to said support wires.

10. An orthodontic face bow appliance, comprising
    (A) an arch wire having an arcuate central portion and opposed legs extending away from said central portion;
    (B) a shield secured to said central portion;
    (C) teeth engaging members carried on the distal ends of said legs of said arch wire; and
    (D) compression springs carried by said legs between said teeth engaging members and said shield.

11. The appliance of claim 10 wherein said shield includes an elongate plastic member disposed on said arch wire.

12. The appliance of claim 10 wherein said shield has an inner and outer face; and a plurality of hooks disposed on said outer face.

13. A method of orthodontic and orthopedic treatment, comprising the steps of:
    (A) applying an intraoral face bow to the teeth and head of the patient; and
    (B) affixing a labial shield to the inner arch wire of the face bow and only projecting in a vertical plane to apply force to the lip muscles and to reduce the force thereof against the teeth to promote anterior growth of the dental arches and align the teeth.

14. The method of claim 13 further characterized by the steps of
    (A) affixing superior and inferior hooks to the inner surface of the shield; and
    (B) applying force in a posterior lineal direction by engaging the interior hooks and selected teeth with an elastic member.

15. The method of claim 14 further characterized by the step of applying force in a vertical direction by engaging the superior hooks and selected teeth with an elastic member.

16. A method of orthodontic and orthopedic treatment, comprising the steps of:
    (A) applying an intraoral face bow to the teeth and head of the patient; and
    (B) affixing a buccal shield to the inner arch wire of the face bow and only projecting in a vertical plane to apply force to the cheek muscles and to reduce the force thereof against the teeth to promote lateral growth of the dental arches and align the teeth.

17. The method of claim 16 further characterized by the steps of
    (A) affixing superior and inferior hooks to the inner surface of the shield; and
    (B) applying force in a posterior lineal direction by engaging the inferior hooks and selected teeth with an elastic member.

18. The method of claim 17 further characterized by the step of applying force in a vertical direction by engaging the superior hooks and selected teeth with an elastic member.

19. A method of correcting malocclusion of teeth; correcting jaw discrepancies; stimulating development of dental arches; and stimulating development of orofacial musculature, comprising the steps of:
    (A) applying an intraoral face bow to the teeth and head of the patient; and
    (B) affixing labial and buccal shields to the face bow and only projecting in a vertical plane to apply force to the lip and cheek muscles and reduce the force thereof against the teeth and promote lateral and anterior growth of the dental arches.

20. The method of claim 19 further characterized by the steps of
    (A) affixing superior and inferior hooks to the inner surface of the shield; and (B) applying force in a posterior lineal direction by engaging the inferior hooks and selected teeth with an elastic member.

21. The method of claim 20 further characterized by the step of applying force in a vertical direction by engaging the superior hooks and selected teeth with an elastic member.

22. The method of claim 19 further characterized by the steps of
   (A) affixing superior and inferior hooks to the inner surface of the shield;
   (B) selectively engaging at least one interior hook with selected teeth by an elastic member; and
   (C) selectively engaging at least one superior hook with selected teeth by an elastic member.

23. A method of orthodontic and orthopedic treatment, comprising the steps of:
   (A) attaching the intraoral activator which includes an arch wire attachment to the teeth of the patient;
   (B) affixing a labial shield to the arch wire of the activator; and
   (C) providing adjustable tension means between the point of attachment of the activator to the teeth and said shield to normally urge said shield against the lip and cheek muscles.

* * * * *